(12) United States Patent
Tsai

(10) Patent No.: US 7,670,035 B2
(45) Date of Patent: Mar. 2, 2010

(54) FRAGRANCE RELEASING ELECTRONIC CANDLE

(75) Inventor: Ching-Tien Tsai, Erlin Township, Changhua County (TW)

(73) Assignee: Chin-Sheng Yang, Tainan (TW)

( * ) Notice: Subject to any disclaimer, the term of this patent is extended or adjusted under 35 U.S.C. 154(b) by 115 days.

(21) Appl. No.: 11/927,789

(22) Filed: Oct. 30, 2007

(65) Prior Publication Data

US 2009/0109663 A1 Apr. 30, 2009

(51) Int. Cl.
*F21V 21/00* (2006.01)
*F21V 35/00* (2006.01)
*F21V 33/00* (2006.01)

(52) U.S. Cl. .................. 362/392; 362/96; 362/161; 362/810

(58) Field of Classification Search .................. 362/810, 362/569, 96, 392, 161
See application file for complete search history.

(56) References Cited

U.S. PATENT DOCUMENTS 7,093,949 B2 * 8/2006 Hart et al. ..................... 362/96
2004/0264169 A1 * 12/2004 Limburg et al. ................ 362/96
2005/0169666 A1 * 8/2005 Porchia et al. .............. 399/111
2005/0169812 A1 * 8/2005 Helf et al. .................... 422/123
2006/0109666 A1 * 5/2006 Tsai ............................ 362/392
2008/0130266 A1 * 6/2008 DeWitt et al. ................. 362/96

* cited by examiner

*Primary Examiner*—Ismael Negron
*Assistant Examiner*—David R Crowe
(74) *Attorney, Agent, or Firm*—Leong C. Lei

(57) ABSTRACT

A fragrance releasing electronic candle comprises a housing constructed in the form of a cylinder and including a circuit board and a battery case, both of which are assembled therein, the battery case including a power switch arranged thereon and a bottom lid covered to the opening thereof, characterized in that the housing includes a receiving compartment formed on the top end thereof for receiving a fragrance piece, and includes a fan secured in the lower side thereof for the connection with the circuit board, the housing also includes an upper cover covered thereon and having a plurality of bores arranged thereon and having a central hole formed at the center thereof for inserting at least one LED lamp therein, such that the at least one LED may be electrically conducted with the circuit board, and a lamp shield in the shape of a flame may be adhesively affixed in the central hole of the upper cover.

2 Claims, 6 Drawing Sheets

FRAGRANCE RELEASING ELECTRONIC CANDLE

BACKGROUND OF THE INVENTION

1. Field of the Invention

The present invention relates to an electronic candle, and more particularly to a fragrance releasing electronic candle that may achieve aesthetic appearance and releasing fragrance.

2. Description of the Prior Arts

A prior art candle is employed for a decoration, a celebration or a religious ceremony, and the like. Nevertheless, a fire may bring about while in use because of carelessness, accordingly a variety of safe candles have been developed in recent days, e.g., an electronic candle, yet such an electronic candle can not release aroma with its illumination.

The present invention has arisen to mitigate and/or obviate the afore-described disadvantages.

SUMMARY OF THE INVENTION

The primary object of the present invention is to provide a fragrance releasing electronic candle that may release different aromas with its illumination.

Another object of the present invention is to provide a fragrance releasing electronic candle that may facilitate the replacement of the fragrance piece thereof.

In accordance with one aspect of the present invention, there is provided a fragrance releasing electronic candle comprising:

a housing, an upper cover, a lamp shield, a fan, a circuit board, a battery case, a bottom lid, as well as a fragrance piece, wherein the housing is constructed in the form of a hollow cylinder, and includes an annular shoulder extendedly provided around the inner rim of the top end thereof and having a notch arranged thereon such that a receiving compartment may be formed therein. The receiving compartment includes two LED electricity conducting tabs disposed on the inner sidewall thereof, and includes a support panel mounted on the bottom surface thereof and having meshes arranged thereon. The upper cover includes a plurality of elongated arcuate bores formed on the top surface thereof, and includes a central hole fixed at the center thereof for inserting two different heights of LED lamps therein, and includes two LED electricity conducting members secured on the internal surface thereof for conducting with the LED lamps individually. The lamp shield is constructed in the form of a flame, and includes an inserting segment affixed on the lower end thereof. In addition, the fan includes a female connector couplingly fixed thereon, and the circuit board contains a male connector couplingly attached thereon for corresponding to the female connector of the fan. Further, the battery case includes a bottom plate extendedly secured around the periphery of the lower end thereof and having a power switch and a socket, both of which are arranged thereon. It is to be noted that the power switch may be operated in a manual, vibrating or a light sensing manner. The bottom plate includes three offset pegs extendedly fixed on the bottom surface thereof. Besides, the fragrance piece is constructed in the shape of a circle in response to the receiving compartment of the housing.

In operation, the power switch is turned on so that the batteries and the circuit board conductively contact with each other, thus controlling the LED lamps to emit in a specific manner, and then the emitting lights pass through the lamp shield to illuminate as a substantial candle. In the meantime, the circuit board may control the fan to operate, and by using the meshes of the support panel, the fragrance piece release aroma outwardly from the bores of the upper cover.

The present invention will become more obvious from the following description when taken in connection with the accompanying drawings, which show, for purpose of illustrations only, the preferred embodiment in accordance with the present invention.

DETAILED DESCRIPTION OF THE PREFERRED EMBODIMENT

Figure 1:
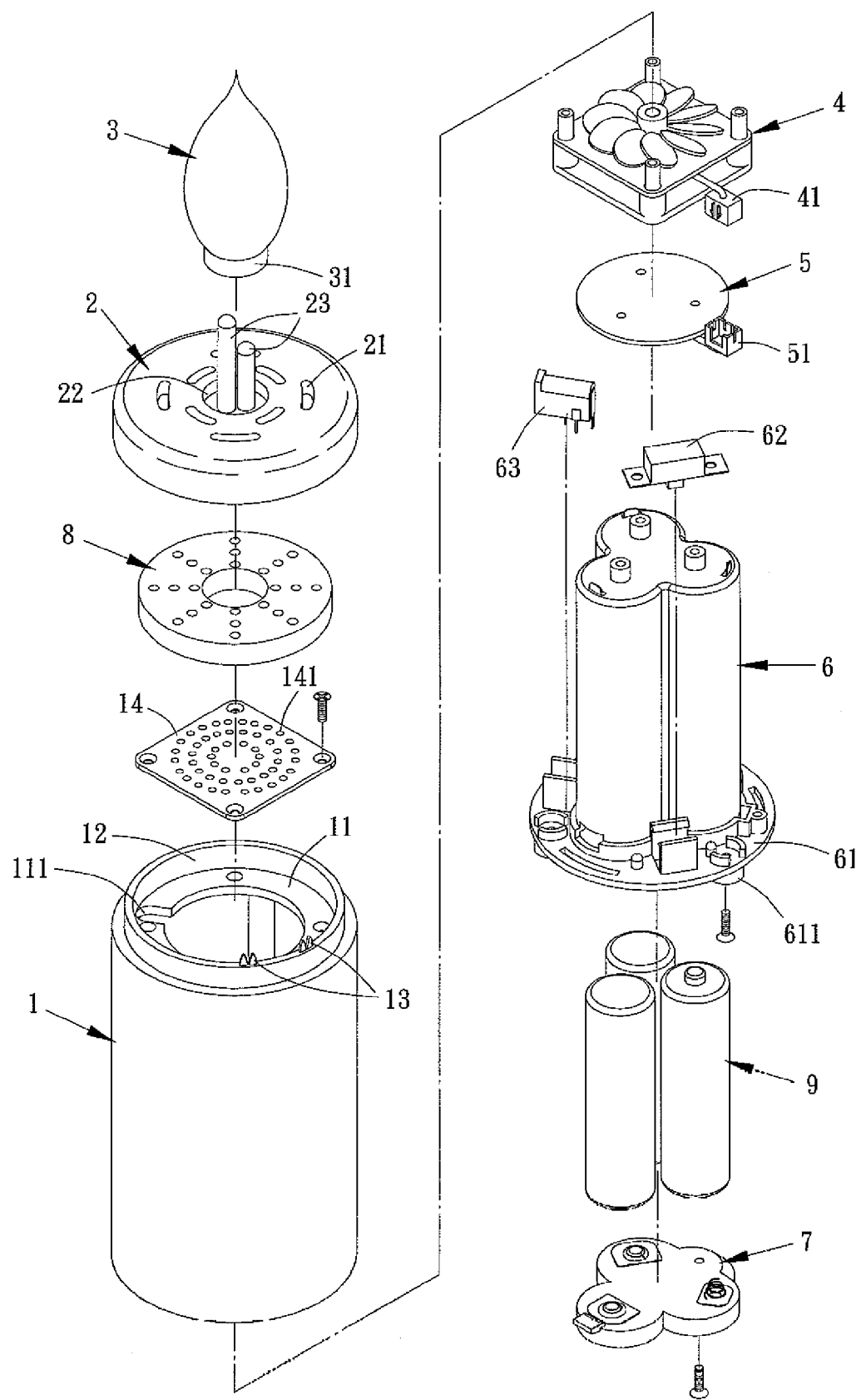
FIG. 1 is a perspective diagram illustrating the exploded components of a fragrance releasing electronic candle according to the present invention.
Figure 2:
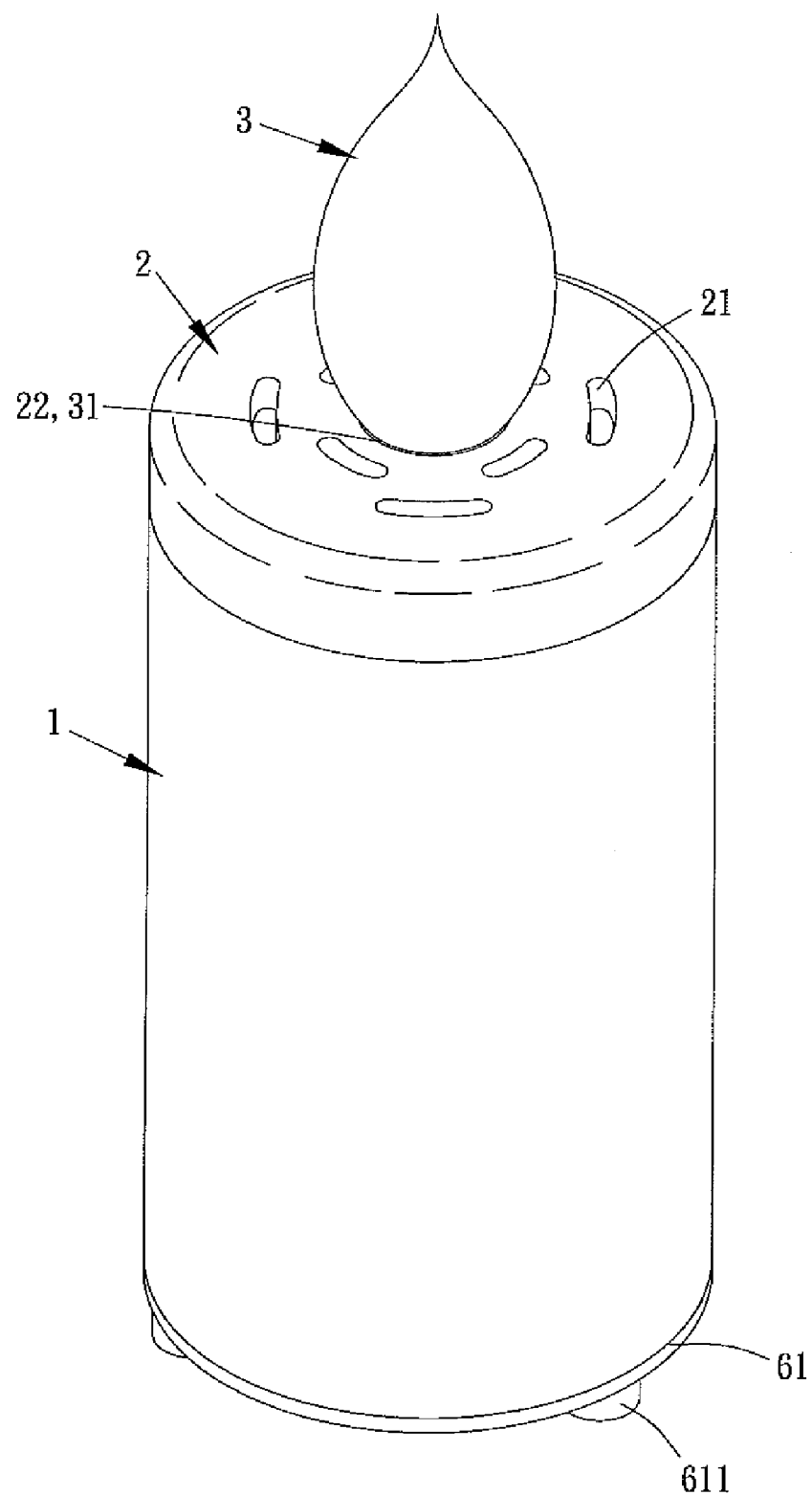
FIG. 2 is a perspective diagram illustrating the assembly of the fragrance releasing electronic candle according to the present invention.
Figure 3:
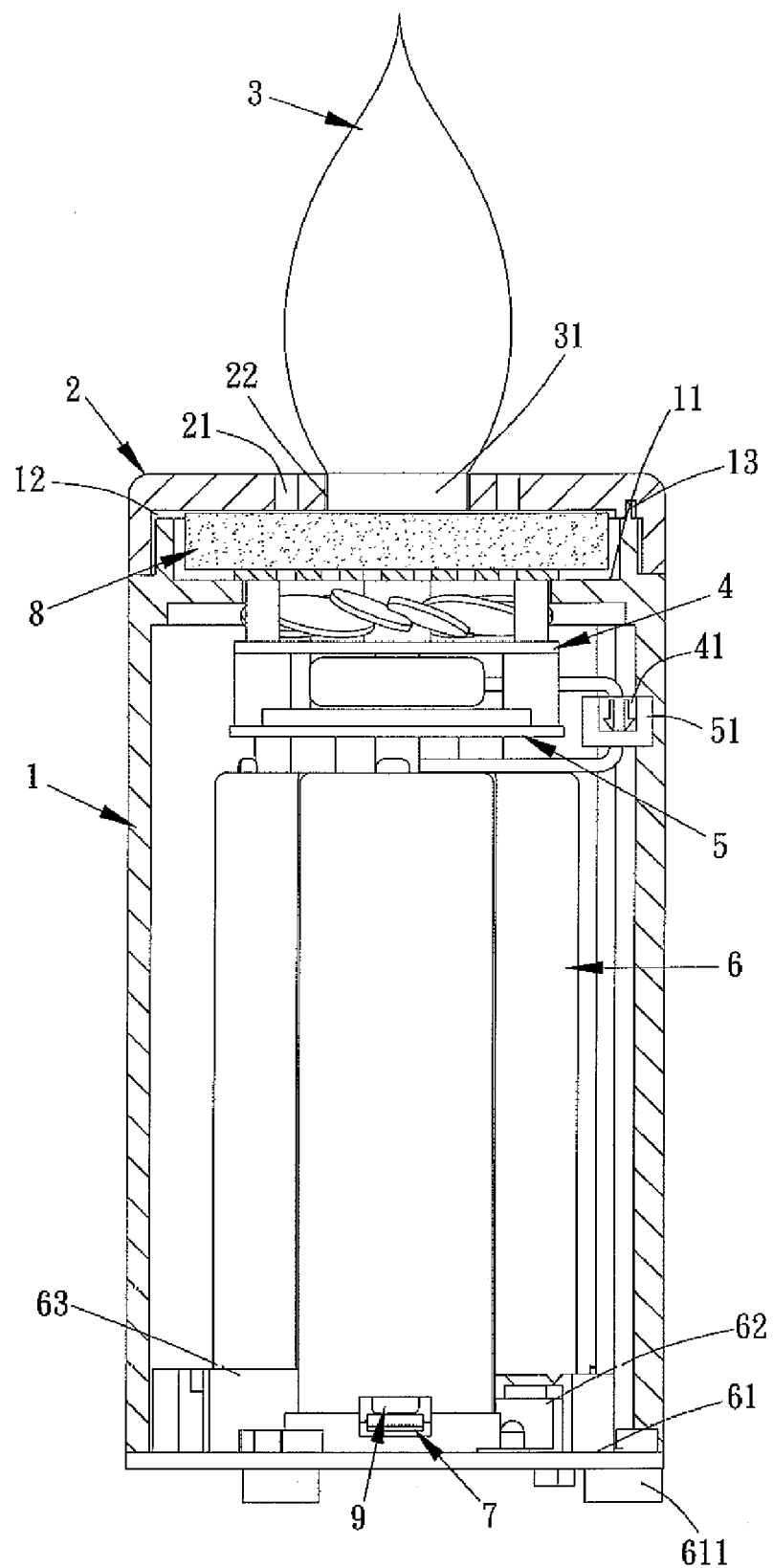
FIG. 3 is a cross sectional diagram illustrating the assembly of the fragrance releasing electronic candle according to the present invention.

Referring to FIGS. 1-3, a fragrance releasing electronic candle in accordance with the present invention comprises a housing 1, an upper cover 2, a lamp shield 3, a fan 4, a circuit board 5, a battery case 6, a bottom lid 7, as well as a fragrance piece 8, wherein the housing 1 is constructed in the form of a hollow cylinder, and includes an annular shoulder 11 extendedly provided around the inner rim of the top end thereof and having a notch 111 arranged thereon such that a receiving compartment 12 may be formed therein. The receiving compartment 12 includes two LED electricity conducting tabs 13 disposed on the inner sidewall thereof, and includes a support panel 14 mounted on the bottom surface thereof and having meshes 141 arranged thereon. The upper cover 2 includes a plurality of elongated arcuate bores 21 formed on the top surface thereof and includes a central hole 22 fixed at the center thereof for inserting two different heights of LED lamps 23 therein, and includes two LED electricity conducting members secured on the internal surface thereof for conducting with the LED lamps 23 individually. The lamp shield 3 is constructed in the form of a flame, and includes an inserting segment 31 affixed on the lower end thereof. In addition, the fan 4 includes a female connector 41 couplingly fixed thereon, and the circuit board 5 contains a male connector 51 couplingly attached thereon for corresponding to the female connector 41 of the fan 4. Further, the battery case 6 includes a bottom plate 61 extendedly secured around the periphery of the lower end thereof and having a power switch 62 and a socket 63, both of which are arranged thereon. It is to be noted that the power switch 62 may be operated in a manual, vibrating or a light sensing manner. The bottom plate 61 includes three offset pegs 611 extendedly fixed on the bottom surface thereof. Besides, the fragrance piece 8 is constructed in the shape of a circle in response to the receiving compartment 12 of the housing 1.

In assembly, the fan 4 is disposed below the lower side of the receiving compartment 12 of the housing 1, and the circuit board 5 is connected with the top surface of the battery case 6 and is placed into the housing 1 with the battery case 6, hence the circuit board 5 is electrically conducted with the two LED electricity conducting tabs 13, and the male connector 51 thereof and the female connector 41 of the fan 4 are coupled with each other, and the bottom plate 61 of the battery case 6 abuts against the bottom of the housing 1. Furthermore, the battery case 6 is provided to receive cylindrical batteries therein, and a bottom lid 7 is used to engageably cover the opening of the battery case 6, the fragrance piece 8 is placed on the support panel 14 in the receiving compartment 12 of the housing 1, and then the inserting segment 31 is inserted through the central hole 22 of the upper cover 2 for being adhesively affixed, such that the two LED lamps 23 are received in the lamp shield 3, and the upper cover 2 is covered on the upper end of the housing 1. Thereby, the two LED electricity conducting members on the internal surface of the upper cover 2 conductively contact with the two LED electricity conducting tabs 13 of the housing 1 respectively, finishing the assembly.

Figure 4:
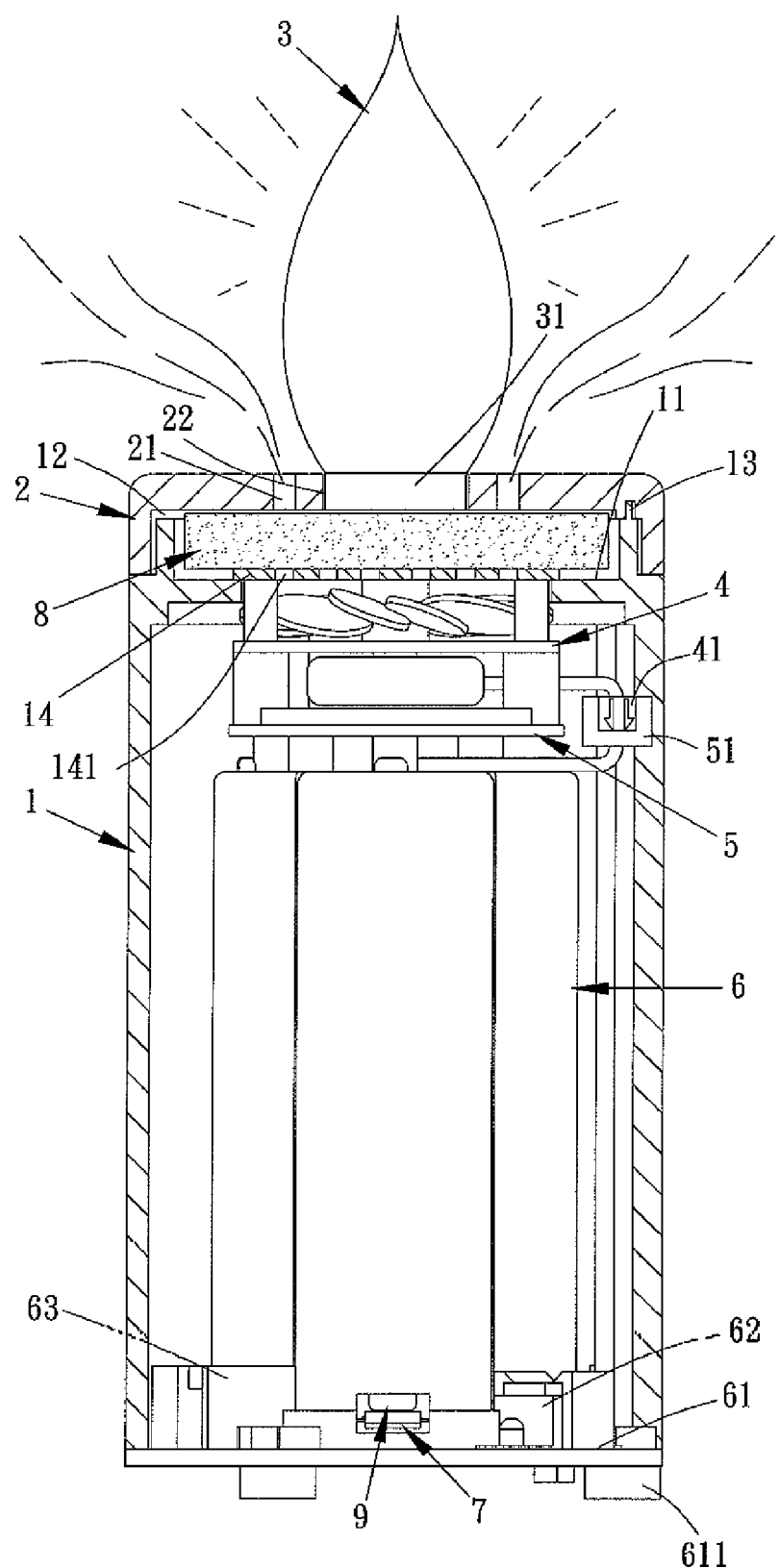
FIG. 4 is a cross sectional diagram illustrating the operating state of the fragrance releasing electronic candle according to the present invention.

In operation, as shown in FIG. 4, the power switch 62 is turned on so that the batteries 9 and the circuit board 5 conductively contact with each other so as to control the LED lamps 23 to emit in a specific manner, and then the emitting lights pass through the lamp shield 3 to illuminate as a substantial candle. In the meantime, the circuit board 5 may control the fan 4 to operate, and by using the meshes 141 of the support panel 14, the fragrance piece 8 releases aroma outwardly from the bores 21 of the upper cover 2.

Figure 5:
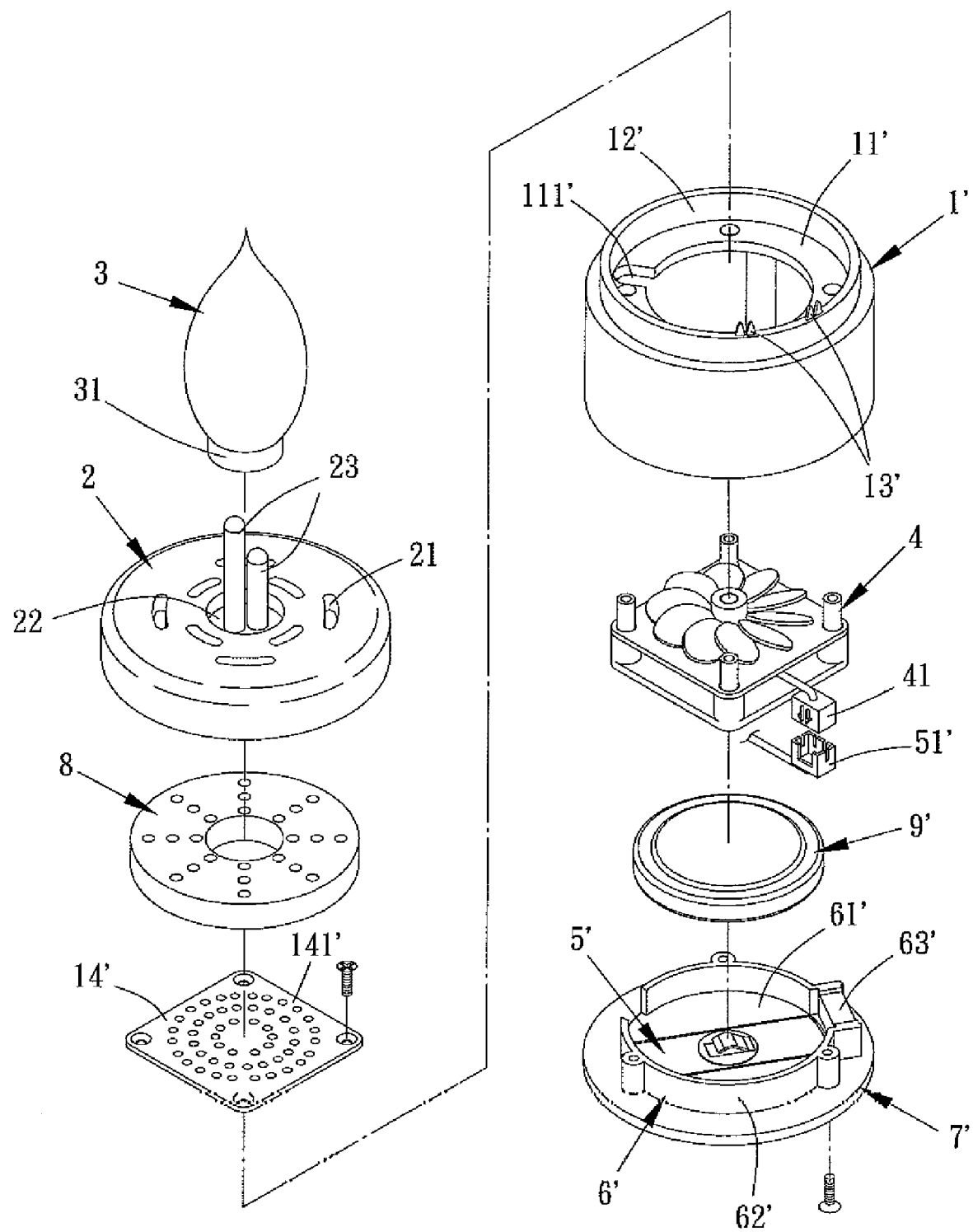
FIG. 5 is a perspective diagram illustrating the exploded components of a fragrance releasing electronic candle according to another embodiment of the present invention.
Figure 6:
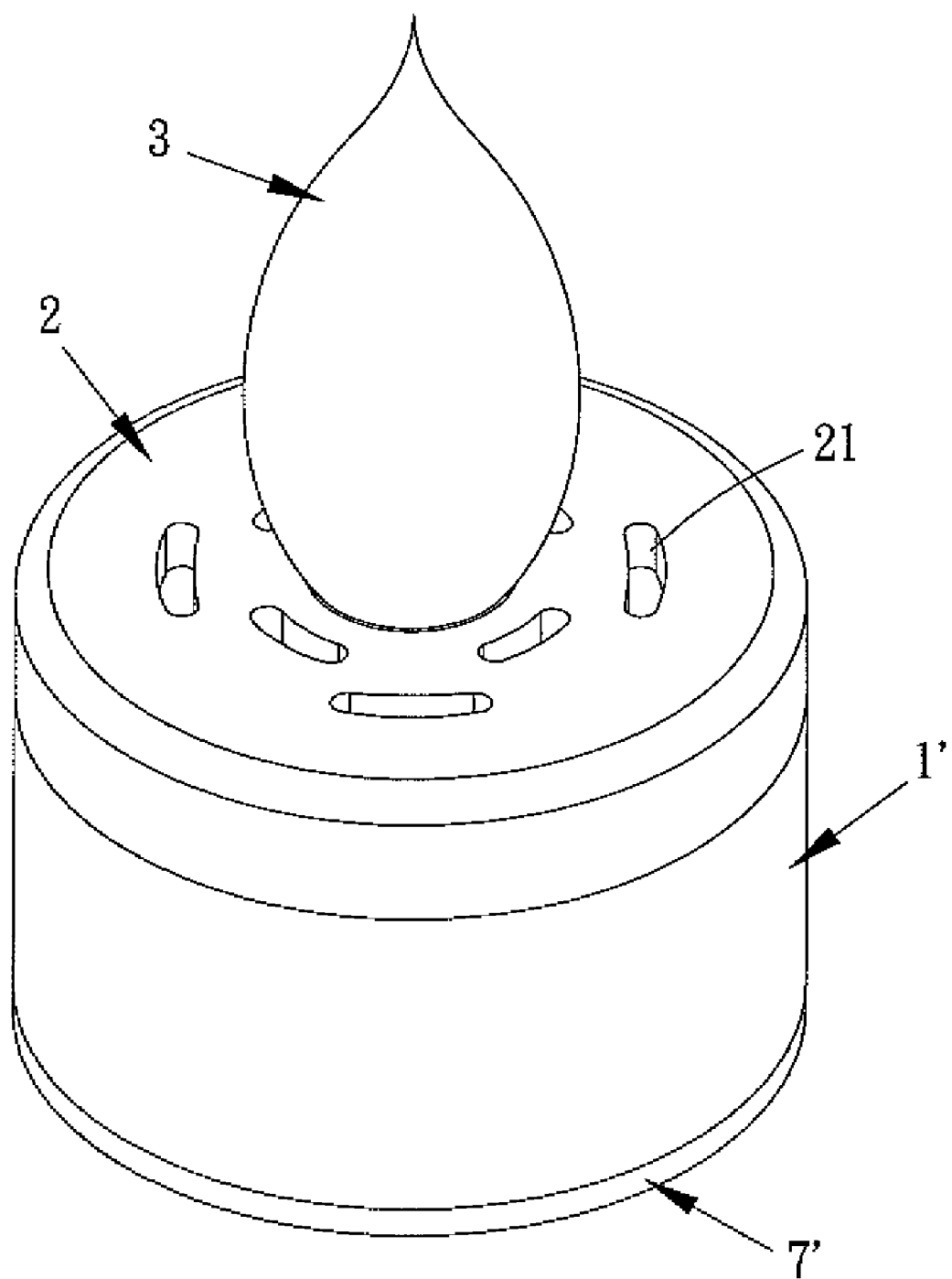
FIG. 6 is a perspective diagram illustrating the assembly of the fragrance releasing electronic candle according to another embodiment of the present invention.

Referring to FIGS. 5 and 6, a fragrance releasing electronic candle in accordance with another embodiment of the present invention comprises a housing 1', an upper cover 2, a lamp shield 3, a fan 4, a circuit board 5', a cell case 6', a bottom lid 7', as well as a fragrance piece 8, wherein the housing 1' is constructed in the form of a hollow short column, and includes an annular shoulder 11' extendedly provided around the inner rim of the top end thereof and having a notch 111' arranged thereon such that a receiving compartment 12' may be formed therein. The receiving compartment 12' includes two LED electricity conducting tabs 13' disposed on the inner sidewall thereof and includes a support panel 14' mounted on the bottom surface thereof and having meshes 141' arranged thereon. The upper cover 2 includes a plurality of elongated arcuate bores 21 formed on the top surface thereof, and includes a central hole 22 fixed at the center thereof for inserting two different heights of LED lamps 23 therein, and includes two LED electricity conducting members secured on the internal surface thereof for conducting with the LED lamps 23 individually. The lamp shield 3 is constructed in the form of a flame, and includes an inserting segment 31 affixed on the lower end thereof. In addition, the fan 4 includes a female connector 41 couplingly fixed thereon, and the circuit board 5, contains a male connector 51' couplingly attached thereon for corresponding to the female connector 41 of the fan 4. Further, the cell case 6' includes a circular plate 61' formed therein and having an annular projection 62' affixed thereon and extending outwardly therefrom for coupling with a power switch 63'. It is to be noted that the power switch 63' may be operated in a manual, vibrating or a light sensing manner. Besides, the fragrance piece 8 is constructed in the shape of a circle for corresponding to the receiving compartment 12' of the housing 1'.

In assembly, the fan 4 is disposed below the lower side of the receiving compartment 12' of the housing 1', and the circuit board 5' is placed on the circular plate 61' of the cell case 6', hence the circuit board 5' is locked on the bottom lid 7' with the cell case 6', and the male connector 51' thereof and the female connector 41 of the fan 4 are coupled with each other. Furthermore, the cell case 6' is provided to receive a mercury cell 9' therein, and the bottom lid 7' is used to engageably cover the bottom of the housing 1', the fragrance piece 8 is placed on the support panel 14' in the receiving compartment 12' of the housing 1', and the inserting segment 31 is inserted through the central hole 22 of the upper cover 2 for being adhesively affixed, such that the two LED lamps 23 are received in the lamp shield 3, and the upper cover 2 is covered on the upper end of the housing 1. Thereby, the two LED electricity conducting members on the internal surface of the upper cover 2 conductively contact with the two LED electricity conducting tabs 13' of the housing 1' respectively, finishing the assembly.

It can be clearly seen from the preceding accounts on the features of the present invention that the fragrance releasing electronic candle of the present invention has the following advantages:
1. The fragrance releasing electronic candle not only may obtain a candle-like realistic purpose while emitting lights, but also may avoid the danger of fire.
2. The fragrance piece 8 may be replaced based on requirement, releasing different aromas. Likewise, while in such a replacement, the upper cover 2 may be removed from the housing 1, 1', facilitating the replacement of the fragrance piece 8.

The invention is not limited to the above embodiment but various modifications thereof may be made. It will be understood by those skilled in the art that various changes in form and detail may be made without departing from the scope and spirit of the present invention.

What is claimed is:

1. A fragrance releasing electronic candle comprising:
   a cylindrical housing having an annular shoulder provided around an inner rim of a top end of said cylindrical housing thereby forming a receiving compartment between said annular shoulder and an open top of said cylindrical housing, said receiving compartment being provided with two electricity conducting tabs;
   an upper cover having a top formed with a central hole and a plurality of elongated arcuate bores, said upper cover being provided with two LED electricity conducting members;
   a lamp shield having a lower end provided with an inserting segment inserted through said central hole of said upper cover and adhesively affixed to said central hole of said upper cover;
   two LED lamps of different heights fitted in said central hole of said upper cover and enclosed by said lamp shield, said LED lamps being electrically connected with said two LED electricity conducting members;
   a support panel mounted on said annular shoulder and provided with a plurality of meshes;
   a fragrance piece disposed on said support panel;
   a battery case fitted in said housing;
   a circuit board mounted on at top of said battery case and provided with a male connector, said circuit board being electrically connected with said two LED electricity conducting tabs;
   a fan arranged on said circuit board and disposed under said support panel, said fan being provided with a female connector engaged with said male connector of said circuit board;
   batteries fitted in said battery case; and
   a bottom lid engaged with a bottom of said battery case.

2. The fragrance releasing electronic candle as claimed in claim 1, wherein said bottom lid is provided with a power switch.

* * * * *